United States Patent [19]

Eibofner

[11] 4,294,797

[45] Oct. 13, 1981

[54] SERVICING COMPOSITION FOR SPRAYING ON MEDICAL INSTRUMENTS

[75] Inventor: Eugen Eibofner, Biberach, Fed. Rep. of Germany

[73] Assignee: Kaltenbach & Voight GmbH & Co., Fed. Rep. of Germany

[21] Appl. No.: 141,363

[22] Filed: Apr. 18, 1980

[30] Foreign Application Priority Data

Apr. 24, 1979 [DE] Fed. Rep. of Germany ....... 2916552

[51] Int. Cl.³ ............................................ A01N 31/00
[52] U.S. Cl. ....................................... 422/36; 252/11; 422/29; 424/333; 424/334; 424/343
[58] Field of Search ............... 422/29, 36, 28; 252/11; 424/333, 334

[56] References Cited

U.S. PATENT DOCUMENTS

| | | | |
|---|---|---|---|
| 2,457,500 | 12/1948 | Sandura | 422/28 X |
| 3,364,068 | 1/1968 | Stern | 422/36 X |
| 3,457,031 | 7/1969 | Linder et al. | |
| 3,515,671 | 6/1970 | Adams et al. | 424/333 X |
| 3,787,566 | 1/1974 | Gauvreau | 424/333 X |
| 3,912,450 | 10/1975 | Boscher | 422/36 X |
| 3,983,252 | 9/1976 | Buchalter | 422/36 X |
| 4,082,852 | 4/1978 | Heiss | 424/333 X |

FOREIGN PATENT DOCUMENTS

| | | | |
|---|---|---|---|
| 700115 | 11/1953 | United Kingdom . | |
| 778240 | 7/1957 | United Kingdom . | |
| 778358 | 7/1957 | United Kingdom . | |
| 936677 | 9/1963 | United Kingdom | 424/333 |
| 992813 | 5/1965 | United Kingdom . | |
| 1499448 | 2/1970 | United Kingdom . | |
| 1214523 | 12/1970 | United Kingdom . | |
| 1342530 | 1/1974 | United Kingdom . | |
| 1457509 | 12/1976 | United Kingdom | 422/28 |
| 1489769 | 10/1977 | United Kingdom . | |

*Primary Examiner*—Barry Richman
*Attorney, Agent, or Firm*—Scully, Scott, Murphy & Presser

[57] ABSTRACT

A servicing composition which is sprayed from a container on or into a medical instrument e.g. a dental handpiece. The servicing composition includes an oil and propellant mixture for lubrication purposes but, for improved sterilizing purposes during subsequent hot-air heating and sterilizing of a medical instrument, an alcohol-aldehyde active substance combination in a proportion of 5 to 15% by weight is added to the mixture which is sprayed on the instrument. The preferred alcohol is isopropanol and the preferred aldehyde is formaldehyde or a succinic acid dialdehyde complex, and the preferred ratio of alcohol to aldehyde is 1:1.

1 Claim, 1 Drawing Figure

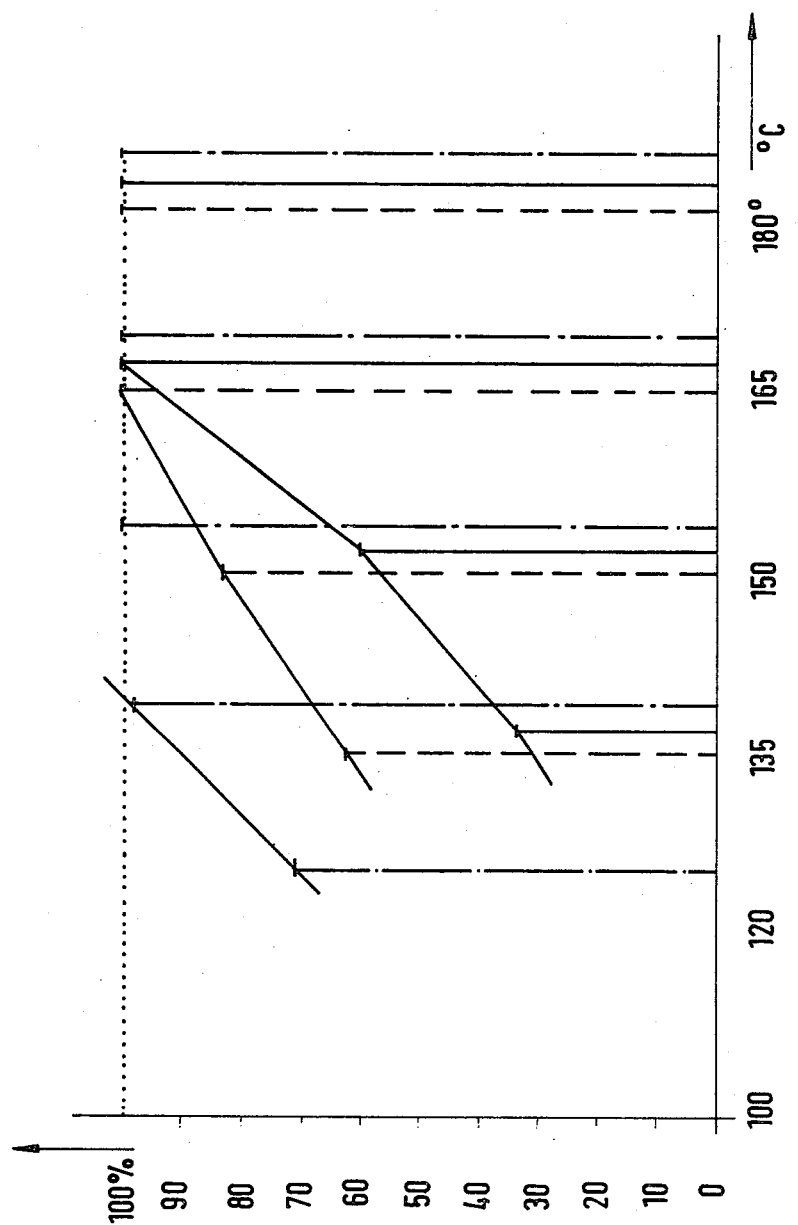

SERVICING COMPOSITION FOR SPRAYING ON MEDICAL INSTRUMENTS

This invention relates to a servicing composition for spraying on medical instruments, particularly dental handpieces and angle-pieces, and including a mixture of oil and a propellant.

Servicing compositions, known by way of example from German Pat. Nos. 20 53 219 and 22 49 886, with addition of a vaporizable solvent, can be used to distribute an initially relatively thin-flow lubricant film uniformly on all inner elements, (particularly bearings) of a medical instrument. When vaporization of the solvent takes place, there remains a lubrication oil film covering all elements with uniform thickness. However, the rinsing or cleansing effect with such a servicing compound is, in the case of multi-part medical instruments, (in particular in the case of dental hand pieces and angle pieces having driving and bearing means in the interior for driving the implements) not so comprehensive that all the soiling substances which have penetrated into the instrument can be reliably removed from the instrument. Examples of soiling substances typically encountered with dental instruments include tooth and emery dust, saliva, blood and the like, with the pathogenic micro-organisms or germs contained therein, such as viri, bacteria, and spores. In particular, in the case of surgical operations, but also in the case of preserving treatment on the patient, the doctor or dentist is compelled, in order to prevent the transfer of infections diseases, to keep quite definitely sterile all instruments coming into contact with the patient.

Now, in order to keep medical instruments, in particular dental hand-pieces or angle pieces, free from causes of infection, it has already been proposed in German Pat. No. 561 205 to dip the instruments, partially assembled, into a cleansing or sterilizing liquid and to convey the said liquid by means of compressed air into the interior of the instruments, so as thereby to flush out the impurities, and to effect re-oiling either simultaneously by means of the cleansing or sterilizing liquid or by subsequent spraying-in of lubricants after the cleansing process. Apart from the fact that the necessary partial disassembly of the medical instrument is unpleasant or inconvenient for the doctor, it is not possible to speak here of true sterilization of the instruments, since for this purpose the additional application of more or less high temperatures is always necessary. With the cleansing or alleged sterilization liquid indicated in this specification, for example petrol or benzene, it is possible to achieve at most a certain degree of disinfection of the instruments.

Furthermore, there has, for the true sterilization of medical and dental instruments, become known an apparatus operating in the manner of an autoclave system, whereby the instruments are subjected during a predetermined period of time to a dry gas arising from a chemical liquid under the influence of heat and subjected to pressure, at a temperature of approximately 125° C. to 130° C. Since, in the case of this device, work is not done with hot water or steam, it is true that there is no risk of rust formation or the formation of other harmful changes of the instruments produced by corrosion. In the case of multi-part instruments, such as for example dental hand pieces and angle pieces, however, the sterilization effect is unsatisfactory, since the pathogenic materials are screened in the interior of the instrument by dirt and possibly by a high-temperature-resisting oil, so that the gas accelerating the sterilization effect does not reach them. Also with this device, therefore, the desired optimum sterility of the instruments is not achievable.

The present invention seeks to provide a servicing composition which can eliminate the above-mentioned defects and which enables the cleansing of multi-part medical instruments, in particular dental handpieces and angle pieces (having driving and bearing means arranged in the interior for the driving of implements coupled with the instruments) without disassembling them into their individual elements, in one working step, then lubrication and subsequently under the influence of heat, by way of example in an autoclave or by means of hot air, sterilization in optimum fashion. In this way, the result is to be achieved that the sterilization temperature and the time requirement is substantially diminished relative to the hitherto-known servicing and sterilization measures, without the lubricating effect of the oil being impaired by the sterilization process.

According to the invention there is provided a servicing composition for spraying on medical instruments in order to lubricate and sterilize the latter, the composition comprising:

a mixture of an oil and a propellant for lubrication purposes, and a sterilizing agent added to said mixture for sterilization purposes;

in which the sterilizing agent compises an alcohol-aldehyde active substance combination in a proportion 5 to 15% by weight of the servicing composition.

The advantages achievable by the invention are above all to be seen to reside in the fact that the sterilization effect of the alcohol-aldehyde active substance combination or components, passing with the servicing composition, to all locations with risk of soiling, into the interior of the medical instrument and into direct contact with the pathogenic material, and which to some extent represent a sterilization-aid, is greatly increased by the heat, so that in the case of a relatively short treatment duration all germs can be killed or all microorganisms destroyed, i.e. above all also such as are sealed off by the active substance combination according to the invention from direct influence of steam or hot air. In particular—as practice has shown—the sterilization time can be considerably reduced as compared with current known sterilizing procedures, for example under the same conditions from 45 to 15 min., so that in the same time more medical instruments can be treated. Additionally, it is possible to considerably reduce also the treatment temperature for an optimum sterilization effect.

Examples of a servicing composition according to the invention will now be described in detail.

The servicing composition includes oil and a propellant which serves for the spraying of lubricating material from a container on and/or into the interior of the medical instrument which is to be cleaned and sterilized and lubricated. The oil and the propellant may be selected from the oil and propellant constituents of known servicing compositions e.g. as disclosed in German Pat. Nos. 20 53 219 and 22 49 886. The oil is present in the servicing composition in a proportion of 10 to 30% by weight, and the propellant is present in a proportion of approximately 20% by weight.

To the mixture of oil and propellant, there is added a sterilizing agent in the form of an alcohol-aldehyde active substance combination which is present in a proportion of 5 to 15% by weight. The preferred alcohol is isopropanol, and the aldehyde may be formaldehyde or a succinic acid dialdehyde complex. The preferred ratio of alcohol to aldehyde is 1:1.

Other combinations of alcohol-aldehyde mixtures may be adopted as desired.

Preferably, the servicing composition also includes a cleansing agent, which comprises any suitable conventional cleansing agent as used in the cleaning and sterilizing of medical and dental instruments. The cleansing agent is present in a proportion of approximately 50% by weight.

The efficacy of a servicing composition according to the invention will be apparent from the accompanying drawing which is a graph of treatment temperature against degree of sterility which is achievable during sterilization by hot air subsequent to spray-application of the servicing composition to a medical instrument.

The graph illustrates a reduction in treatment temperature which may be achieved for a servicing composition according to the invention, during subsequent sterilization by hot air, as compared with known servicing compositions. The graph has been plotted for the same holding times in respect of each servicing composition. The full lines relate to the presence of a conventional servicing composition, the broken lines to emission of a servicing composition, and the dot-dash lines to a servicing composition according to the invention.

Since, in the case of the servicing composition according to the invention, the active substance combination vaporizes under the heat effect, the oil remains back in unchanged form at the applied locations in the interior of a dental instrument and is therewith completely capable of lubrication.

I claim:

1. A method of lubricating and sterilizing a medical instrument comprising: spraying a servicing composition on said instrument so that the latter is wetted internally and externally with the servicing composition, said composition comprising a mixture of a lubricating oil and a propellant, and a sterilizing agent added to said mixture and comprising an isopropanol-aldehyde active substance combination in a proportion of 5 to 15% by weight of the servicing composition wherein the aldehyde is selected from the group consisting of formaldehyde and a succinic acid dialdehyde complex;

and heating the medical instrument, so as to increase the sterilizing effect of said active substance combination, until the active substance combination has vaporized.

* * * * *